United States Patent
Yarbrough et al.

(10) Patent No.: US 9,266,801 B2
(45) Date of Patent: Feb. 23, 2016

(54) OLEFIN HYDRATION PROCESS

(75) Inventors: Charles Morris Yarbrough, Baton Rouge, LA (US); Seth McConkie Washburn, Houston, TX (US); Dennis Jay Davoren, Baton Rouge, LA (US); Michael Alan Better, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 318 days.

(21) Appl. No.: 13/382,790

(22) PCT Filed: Jun. 17, 2010

(86) PCT No.: PCT/US2010/038921
§ 371 (c)(1),
(2), (4) Date: Mar. 26, 2012

(87) PCT Pub. No.: WO2011/014309
PCT Pub. Date: Feb. 3, 2011

(65) Prior Publication Data
US 2012/0172635 A1    Jul. 5, 2012

Related U.S. Application Data

(60) Provisional application No. 61/229,978, filed on Jul. 30, 2009.

(51) Int. Cl.
*C07C 29/06*    (2006.01)
*C07C 29/10*    (2006.01)

(52) U.S. Cl.
CPC .............. *C07C 29/06* (2013.01); *C07C 29/10* (2013.01)

(58) Field of Classification Search
CPC ..................................................... C07C 29/06
USPC ........................................ 568/893, 895, 899
See application file for complete search history.

(56) References Cited

U.S. PATENT DOCUMENTS

| 2,050,442 A | | 8/1936 | Metzger | |
| 2,109,004 A | | 2/1938 | Archibald et al. | |
| 2,533,808 A | * | 12/1950 | Howlett | 568/889 |
| 4,393,256 A | * | 7/1983 | Schmidt | 568/907 |
| 4,405,822 A | | 9/1983 | Bezman | |
| 4,579,984 A | * | 4/1986 | Neier | C07C 29/04 568/895 |
| 5,569,789 A | | 10/1996 | Bell et al. | |
| 6,906,229 B1 | | 6/2005 | Burton | |
| 7,399,891 B2 | | 7/2008 | Yarbrough et al. | |

FOREIGN PATENT DOCUMENTS

| GB | 642905 | 9/1950 |
| GB | 763544 | 12/1956 |

* cited by examiner

*Primary Examiner* — Scarlett Goon
*Assistant Examiner* — Sonya Wright

(57) ABSTRACT

The invention is directed to improvements in the indirect hydration process for the production of alcohols that enable high alcohol yield by increasing ether recycle in an olefin hydration process, such as the hydration process to produce isopropyl alcohol (IPA) from propylene or the hydration process to produce sec-butyl alcohol (SBA) from butylene.

4 Claims, 3 Drawing Sheets

IPA/IPE reaction system

SBA/SBE reaction system

IPA/IPE reaction system

OLEFIN HYDRATION PROCESS

CROSS REFERENCE TO RELATED APPLICATIONS

This application is a National Stage Application of International Application No. PCT/US2010/038921, filed Jun. 17, 2010, which claims the benefit of prior U.S. Provisional Application Ser. No. 61/229,978, filed Jul. 30, 2009, which are hereby incorporated by reference in their entireties.

FIELD OF THE INVENTION

The invention relates to olefin hydration processes and more specifically to ether recycle process improvements for olefin hydration processes.

BACKGROUND OF THE INVENTION

Commercial olefin hydration processes react water with an olefin over an acid catalyst to produce alcohols. These processes also produce a co-product ether. These ethers are dialkyl ethers of the olefin being fed. By way of example, when propylene is the feed, the ether is di-isopropyl ether (IPE), and for butenes it is di-secondary butyl ether (SBE). The yield of ether produced is determined by the type of hydration process used and the process conditions. For processes that produce isopropyl alcohol (IPA) and secondary butyl alcohol (SBA), ether co-production typically ranges from about 1% to about 15% by weight. Indirect hydration processes, such as those using sulfuric acid, typically produce from about 5% to about 15% by weight ether as a co-product. Direct hydration process which use high purity olefin feeds over solid acid catalyst, such as acid resins, produce less ether but still in the 1 to 7% range. The production of ether reduces the yield of the alcohol; therefore, when alcohol is the desired product it would be advantageous to minimize the amount of ether co-product.

The reaction to produce ether is an equilibrium reaction, e.g., for $C_3$'s (Rxn I) propylene reacts with isopropyl alcohol, over an acidic catalyst, in a reversible reaction to form IPE.

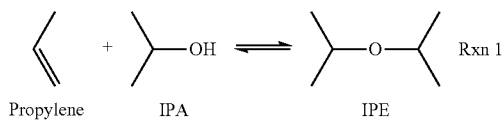

Propylene    IPA    IPE

However, in indirect hydrolysis systems sulfuric acid is used to provide the acidity and forms intermediate esters with the olefin and alcohols. It is also a reversible equilibrium process. Rxn 2-4 below show the reactions of $C_3H_6$ and IPA that form IPE. In order to react recycled IPE there has to be enough sulfuric acid available to reform the alkyl sulfate, the reverse of Rxn 4.

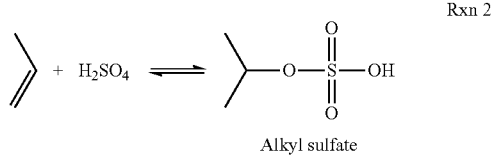

Alkyl sulfate

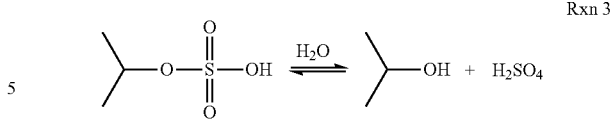

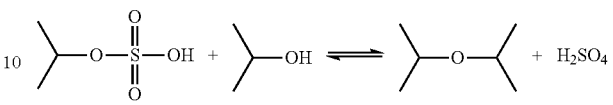

Several methods have been utilized to minimize ether co-product yield. It is possible to minimize ether by reducing the severity of the reaction or to run the reaction in a dilute environment. Another way is to utilize a production method that minimizes ether yield such as in direct hydration. Ether can also be thermally decomposed back to the olefin, it can be decomposed back to the alcohol and an olefin, and it can be recycled back to the hydration reaction step to minimize further production of ether.

The present inventors have discovered methods to maximize ether reversion when it is returned or recycled to the hydration reaction section of the process. These improvements are particularly important for hydration processes that produce >7% by weight ether co-product and/or where the economic value of the ether is lower than the olefin feed stock.

It has been observed that the amount of ether that can effectively be recycled is limited by typical olefin hydration process conditions. In indirect hydration processes conditions are usually mild, i.e., moderate temperatures and pressures, to minimize side reactions. At those conditions the rate of reversion of ether is slow and there is a limited recycling capacity that is available. In fact, only on the order of 20 to 40% can be recycled under those conditions. In a gas absorption process, when ether is fed in excess of this rate it will build up as a liquid phase in the process. This results in unsteady unit operation with ether phase accumulation and results in hydration process unit upsets. Improvements to the recycling process are therefore needed. We have found that by adopting the improvements described here it is possible to greatly increase capability for recycle of ether and hence the yield of the desired alcohol.

Recycle per se has been described in the literature for hydration processes. U.S. Pat. No. 4,579,984 describes a recycle process for a direct hydration process using acid catalyst where the dialkyl ether is introduced into the reaction mixture at a set distance from the outlet of the reactor.

U.S. Pat. Nos. 4,405,822 and 5,569,789 deal with recycling ether to an ether hydrolysis reactor to produce IPA at elevated temperatures and pressures. These are also direct hydration processes and the conditions are not similar to milder indirect hydration conditions.

Recycling ether back to a sulfuric acid system is described in U.S. Pat. No. 2,533,808 and more recently is mentioned in U.S. Pat. No. 7,399,891. However, a recycle according to the present invention is not suggested in the prior art, as far as is known by the present inventors.

The ability to recycle ether into indirect hydration processes has been, heretofore, limited by the mild process conditions that are utilized, by the hydrophobic nature of ether, and by relatively slow absorption rates. These limitations limit the amount of ether that can be normally recycled to only 20-40% of the ether that is produced. This results in limited flexibility to control the ether yield. By careful study of the ether absorption process we have discovered methods to increase absorption of ether up to, in embodiments, 100% or near 100% of that produced. Implementation of these process configurations and conditions will improve the operational stability and yield flexibility of indirect hydration processes.

The present inventors have surprisingly discovered that providing an ether recycle that is substantially vaporized into the reaction vessel(s) substantially overcomes one or more of the aforementioned problem and improved alcohol yield.

SUMMARY OF THE INVENTION

The invention is directed to improvements in process and reactor configuration that enable high percentage ether recycle in the hydration process to produce high yields of alcohol, particularly isopropyl alcohol (IPA) or sec-butyl alcohol (SBA) from propylene (propene) and butylene (butene), respectively, by providing vaporized recycled ether.

In embodiments, systematic application of improved extract saturation through staging, higher acidity, longer reaction times, better mixing, or a combination of two or more of such embodiments, can achieve further increased ether absorption into the acid, so that, in embodiments, improved alcohol production is achieved.

It is an object of the invention to provide an improved method of recycled ether absorption into sulfuric acid in a process for production of alcohol by the indirect hydration of olefins.

It is further an object of the invention to provide high yield of alcohol and 100% or close to 100% recycle of ether in a process for production of alcohol by the indirect hydration of olefins.

These and other objects, features, and advantages will become apparent as reference is made to the following detailed description, preferred embodiments, examples, and appended claims.

DETAILED DESCRIPTION

According to the invention, improvements in the process for the indirect process for the production of alcohols such as IPA and SBA from olefin hydration enable high yield ether recycle.

The present inventors considered that the main problem in the recycle of ether is that the necessary reaction(s) for indirect hydration is slow. This is partially due to the fact that ether is not soluble in sulfuric acid solutions and only absorbs into the acid via the reverse of Rxn 4 above. Equilibrium ether production in indirect hydration processes is about 7 to about 15% by wt of the alcohol produced. At typical reactor conditions; e.g., temperatures of less than about 110° F. (about 43° C.) and pressures less than about 500 psig, only about 30% by weight of the ether produced can be recycled. To enable effective recycle the process must be modified to improve mixing energy and mass transfer.

While temperature and pressure control the reaction rates and equilibrium conditions of the propylene and butylene hydration process, over most of the operating range they have minimal influences on the rate of ether absorption. The present inventors have discovered that it is critical to have appropriate conditions at the ether recycle injection site to allow vaporization of the ether to occur.

Figure 1:
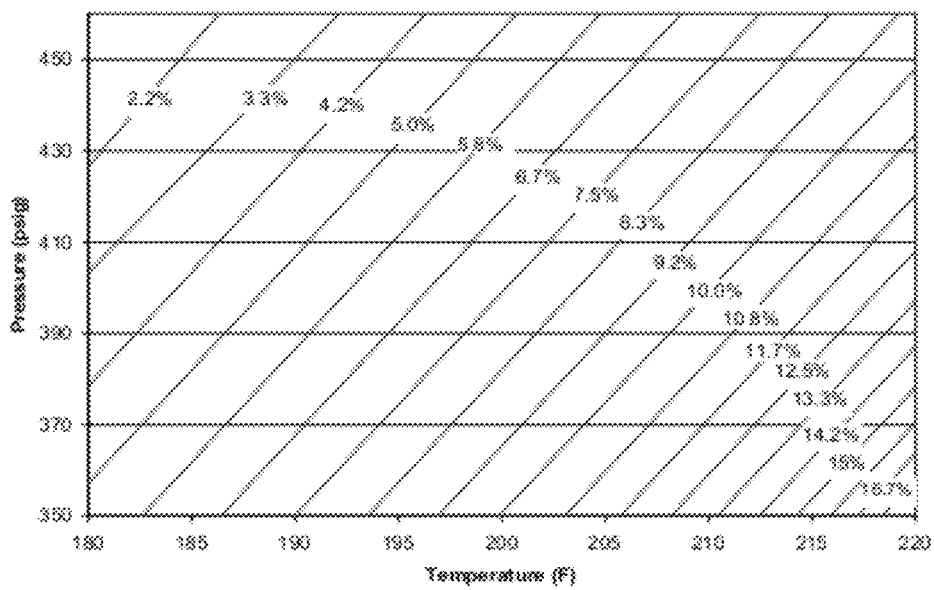
FIG. 1 shows the relationship between the gas and liquid conditions that need to be met to insure vaporization.

FIG. 1 shows the relationship between the gas and liquid conditions that need to be met to insure vaporization. It shows the maximum mass percentage of IPE in a propylene/propane feed that will be completely vaporized at a given temperature and pressure. This vaporization allows increased mixing of the hydrophobic ether into the sulfuric acid extract. Increased mixing via vaporization will maximize ether absorption.

The amount of hydrocarbon absorbed in the acidic solution, referred to as extract saturation ("ES") has a significant effect on the quantity of ether that can be re-absorbed. ES is the ratio of moles of equivalent olefin in the acidic solution over the moles of 100% acid in the solution. As the ES increases the amount of hydrocarbon dissolved in the acid increases and the ability to absorb more hydrocarbon is decreased. The present inventors have discovered that it is important to provide an ES gradient in 2 or more reactor stages to improve the absorption capacity of ether into the sulfuric acid. Lower ES is better for ether absorption. This increases the equilibrium driving force for absorption.

Figure 5:
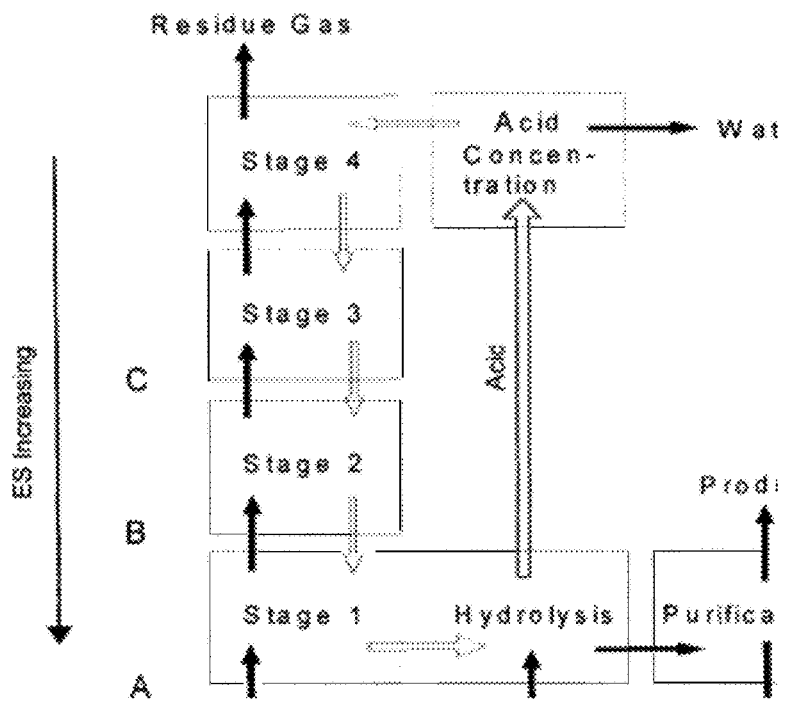
FIG. 5 shows an embodiment of a multistage indirect hydration process where olefin is fed counter current to acid flow.

A multistage indirect hydration process is illustrated schematically in FIG. 5. Olefin feed, propylene/propane or butylene/butane, enters the stage 1 reaction vessel where it contacts sulfuric acid solution coming from stage 2. The olefin continues to flow to stages 2, 3, 4. It will be recognized by one of skill in the art that more or less stages than illustrated may be used. The un-reacted feed or "residue gas" is vented at stage 4 (or the last stage in the sequence). Acid circulates through the stages counter current to the olefin entering at stage 4, or the last olefin stage, and then proceeds to 3, 2, 1 and then to the hydrolysis and purification sections where the product alcohol and ether are recovered. The hydrolysis section uses water to hydrolyze the sulfate esters, Rxn 3 above, and produces alcohol and a diluted sulfuric acid solution. The water diluted acid is sent to the acid concentration section to prepare the acid for recirculation to the reaction stages again, shown as hollow arrows. In embodiment, the present inventors prefer to use at least four stages of decreasing ES to insure better ether re-absorption. This counter-current type process can be used to configure either gas/liquid adsorption or liquid/liquid extraction chemistries.

The aforementioned multistage embodiment provides an opportunity to have two or more ES stages for ether injection. In embodiments, it has been found that it is preferred, for maximum ether absorption, that vaporized ether is injected at a higher ES location such as point A, B and C and then the absorbed ether flows with the olefin, counter-current to the liquid acid phase and contacts a lower ES acid stage to complete the absorption and/or extraction. The ether injection can be made into the vessels themselves or into the olefin feed lines to the vessels. This staging allows more driving force for ether absorption into low ES acid.

The rate of ether absorption is a function of temperature and pressure. The rate of ether absorption is slow at the moderate temperatures, mixing rates and pressure of indirect hydration processes. Therefore, to increase absorption and allow a closer approach to equilibrium it is preferred to increase reaction time where possible. This can be accomplished by increasing residence time by utilizing large reaction vessels or by use of long plug flow plug flow reactors. The use of staging in combination with increased residence time is also a more preferred embodiment, increasing the overall approach to equilibrium.

Figure 2:
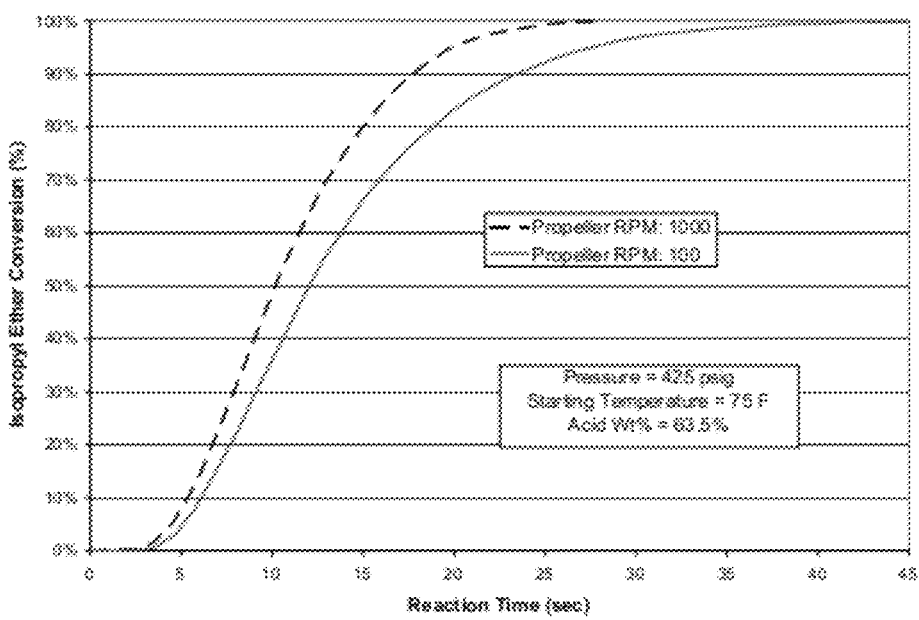
FIG. 2 shows the effect of mixing rates and reaction time on IPE conversion in the hydration process.

In the graph shown in FIG. 2 the relationship just discussed is illustrated. The graph illustrates that even at very low mixing rates and at typical moderate commercial conditions; conversion can be improved by simply increasing the time to react.

Figure 3:
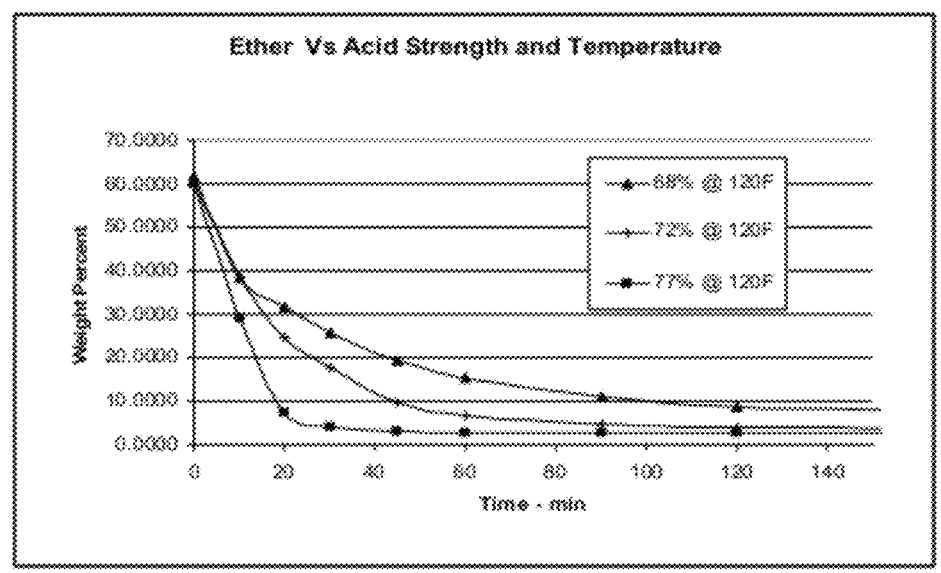
FIGS. 3 and 4 show experimental results for the relationship of acid strength versus solubility of ether for the SBA and IPA system.
Figure 4:
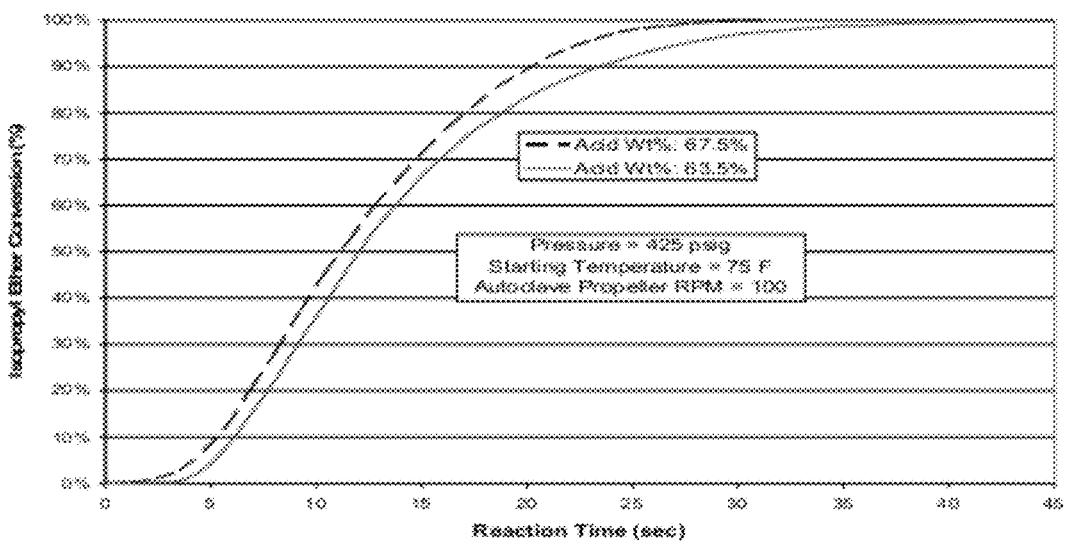

Acid concentration is a significant variable in the adsorption of ether into acid. FIGS. 3 and 4 show experimental results for the relationship of acid concentration versus solubility for the SBA and IPA systems, respectively. In the SBE experiments, FIG. 3, a sulfuric acid solution and SBE (sec-butyl ether) were brought up to temperature separately and then mixed together with moderate stirring. The ether layer on top of the acid was measured visually over time. For the IPE (isopropyl ether) system, FIG. 4, samples of the acid solution and IPE were prepared similarly and combined in an autoclave at pressure. The reaction of IPE and acid is very exothermic. Temperature of the acid was monitored and the temperature curve was used to calculate the reaction progress.

Absorption rates dramatically change over the acid strength range of 60 to 80%. At acid strengths of over about 70% by weight the ether absorption rate is much faster. This discovery provides another avenue for maximizing ether recycling. By recycling the ether to a higher acid strength absorption vessel it can quickly and easily be converted to the acid soluble sulfate ester. That acid vessel does not need to be very large and the acid can then be blended into a circulating process acid process employing a lower acid concentration for the production of alcohols.

Figure 6:
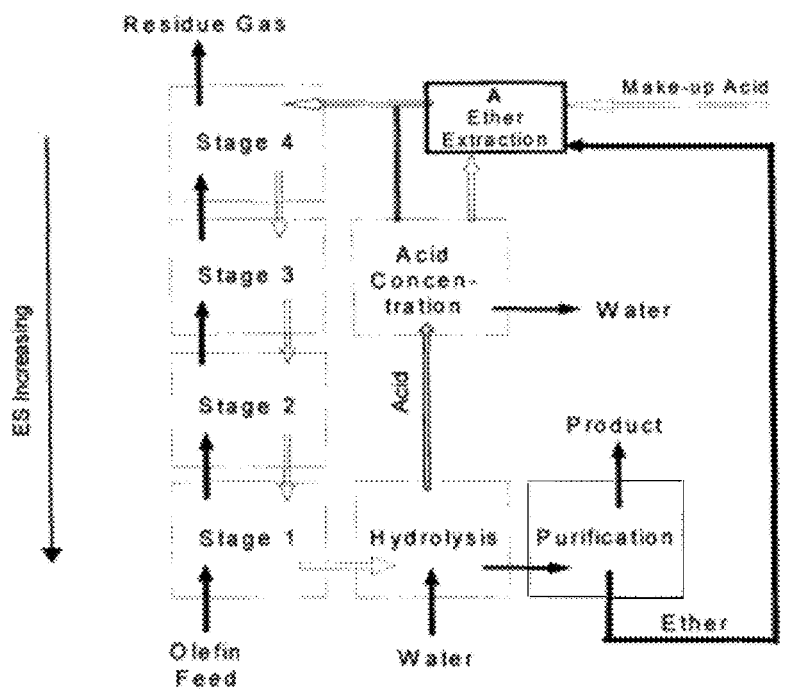
FIG. 6 shows another embodiment of maximizing ether recycling.

This embodiment is illustrated schematically in FIG. 6. Olefin feed, e.g., a propylene/propane or a butylene/butane feed, enters the stage 1 reaction vessel where it contacts sulfuric acid coming from stage 2. The olefin continues to flow to stages 2, 3, and 4. Again it will be recognized by one of skill in the art that more or less stages may be provided, although the present inventors prefer, in embodiments, at least 4 stages. The un-reacted feed or "residue gas" is removed at stage 4 or the last stage in the sequence. The acid phase circulates through the stages counter current to the olefin entering at stage 4 (or the last olefin stage), and then proceeds to 3, 2, 1 and then to the hydrolysis and purification sections where the product alcohol and ether are recovered. The hydrolysis section uses water to hydrolyze the sulfate esters, Rxn 3, and produces alcohol and a diluted sulfuric acid solution. The diluted acid is sent to the acid concentration section to prepare the acid for recirculation to the reaction stages again, shown as hollow arrows. This counter-current type process can be used to configure either gas/liquid adsorption or liquid/liquid extraction chemistries. An additional process step is included that recycles the ether from the purification section to a vessel A containing a higher concentration of acid to facilitate ether absorption. That acid is then blended in with the circulating acid.

FIG. 6 illustrates a process where fresh acid at a slightly higher concentration is used in the absorption vessel, A, Ether Extraction Vessel. One way to do this is to take the typically fresh acid make-up that comes in at high acid concentration, i.e., higher than about 70%, and dilute it to the desired acid concentration using a slip stream of concentrated process acid. Ether is mixed with this acid and is quickly absorbed. This ether extract can then be fed to the unit with the normal concentration recirculation acid. Other means of producing a higher concentration acid, such as those per se known in the art, can be utilized to the same effect.

Both the liquid/liquid and gas/liquid hydration processes require that hydrophobic ethers be absorbed or dissolved in the acid phase to be reacted to alcohol. In the absorption process, inability to absorb ether results in the formation of a separate liquid hydrocarbon phase. This poses two process problems. First, the gas absorption process is configured to provide mixing and contacting between a gas phase and liquid extract phase but not for mixing and contacting between a liquid hydrocarbon and a liquid acid phase. Second the gas absorption process is configured for the counter current movement of the gas and liquid acid phases but not for the counter current movement of two liquid phases. Failure to rapidly vaporize recycled ether in the absorption process will then result in the unsteady state and unstable accumulation of a second liquid phase. The present inventors have found that by the use of significant mixing energy while injecting the ether into the acid, greatly improved absorption can be accomplished. FIG. 2 illustrates the importance of mixing to the absorption process. By going from a stirred two phase system at 100 rpm to a well mixed system at 1000 rpm the time to complete reaction is essentially halved.

Preferred embodiments of the invention include: a process for the production of an aliphatic alcohol by the indirect hydration of an olefin, wherein a co-product of ether is produced, the improvement comprising the recycle of said ether and injection of said ether into said process under sufficient temperature and pressure to provide a vapor of said ether; preferably wherein said sufficient temperature and pressure is determined according to FIG. 1 and/or where said process comprises a multistage adsorption section having counter current flow of olefin feed and sulfuric acid; in embodiments, any of the aforementioned wherein the aliphatic alcohol is isopropyl alcohol or secondary butyl alcohol; in embodiments, wherein the reactor conditions include a temperature of less than 43° C. and a pressure of less than 500 psig; and in a preferred embodiment, any of the aforementioned wherein there is an ES gradiant in 2 or more reactor stages and/or wherein said process comprises a multistage adsorption section having at least 4 stages; and also, in preferred embodiments, any of the aforementioned wherein said vaporization of recycled ether is into an ether absorption vessel having an acid strength of over about 65% by weight, preferably over about 70 wt %, and preferably from over 70 wt % to about 85 wt %.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

One of skill in the art in possession of the present disclosure will appreciate that many variations of the aforementioned invention are possible other than those specifically suggested. All such variations are within the full intended scope of the appended claims.

What is claimed is:

1. A process for the production of an aliphatic alcohol, including the co-production of ether, by the indirect hydration of an olefin in a reactor having a multistage adsorption section with counter current flow of olefin feed and sulfuric acid, comprising the recycle of said ether and injection of said ether into said process under conditions effective to provide said ether as a vapor, wherein there is an extract saturation (ES) gradient in 2 or more reactor stages and said ether is injected at a reactor stage that has a higher ES than the lowest ES location.

2. The process of claim 1, wherein the aliphatic alcohol is isopropyl alcohol.

3. The process of claim 1, wherein the aliphatic alcohol is secondary butyl alcohol.

4. The process of claim 1, wherein the reactor conditions include a temperature of less than 43° C. and a pressure of less than 500 psig.

* * * * *